United States Patent [19]

Toya

[11] Patent Number: 4,853,188
[45] Date of Patent: Aug. 1, 1989

[54] CELL FOR PLACING SOLID MATTERS ON A SLIDE GLASS UNDER CENTRIFUGAL FORCE

[75] Inventor: Matsumi Toya, Koushoku, Japan

[73] Assignees: Kabushiki Kaisha Tiyoda Seisakusho, Koushoku; Sakura Seiki Kabushiki Kaisha, Tokyo, both of Japan

[21] Appl. No.: 294,913

[22] Filed: Jan. 6, 1989

Related U.S. Application Data

[63] Continuation of Ser. No. 930,340, Nov. 12, 1986, abandoned.

[30] Foreign Application Priority Data

Nov. 14, 1985 [JP] Japan ................... 60-174240
Jan. 27, 1986 [JP] Japan ................... 61-8899

[51] Int. Cl.⁴ .............. B01D 33/22; G01N 1/18
[52] U.S. Cl. ...................... 422/104; 422/64;
422/72; 422/102; 436/45; 436/177; 210/361;
210/512.1; 210/781; 210/782; 494/16; 494/20;
427/2; 427/4; 118/50

[58] Field of Search ............... 422/64, 72, 102, 104;
436/45, 177; 118/50; 427/2, 4; 494/16, 20;
210/361, 781, 782, 512.1

[56] References Cited

U.S. PATENT DOCUMENTS

| | | | |
|---|---|---|---|
| 4,197,329 | 4/1980 | Holroyd et al. | 427/2 |
| 4,391,710 | 7/1983 | Gordon | 210/361 |
| 4,468,410 | 8/1984 | Zeya | 427/4 X |
| 4,576,796 | 3/1986 | McCormick | 427/4 X |
| 4,591,486 | 5/1986 | Eberle | 422/72 |
| 4,657,720 | 4/1987 | Inouye | 427/4 X |

FOREIGN PATENT DOCUMENTS 61-170056 10/1986 Japan .

Primary Examiner—Barry S. Richman
Assistant Examiner—Lynn M. Kummert
Attorney, Agent, or Firm—Ladas & Parry

[57] ABSTRACT

A cell for placing solid matter on a piece of slide glass in such a manner that it is rotated in a centrifugal separator, which is formed integrally by mold forming of synthetic resin thereby to be disposable, and a base plate of a cell portion has an elasticity so as to be easily engaged with a hook provided on a holder in which the base plate is held.

20 Claims, 4 Drawing Sheets

CELL FOR PLACING SOLID MATTERS ON A SLIDE GLASS UNDER CENTRIFUGAL FORCE

This is a continuation of co-pending application Ser. No. 930,340 filed on Nov. 12, 1986, now abandoned.

BACKGROUND OF THE INVENTION

This invention relates to a cell for placing solid matter in a liquid on a slide glass under a centrifugal force to prepare a specimen for microscopic examination.

For pathological study or diagnosis, for instance, red blood corpuscles to be examined are taken out of the blood of a patient. At this time, the red blood corpuscles are recovered in such a manner that the red blood corpuscles as solid matter in blood are placed separately from white blood corpuscles on a slide glass set in a centrifugal separator.

To this end, a cell for accommodating blood and for holding the slide glass is used. Such a conventional cell is disclosed in Japanese Utility Model Laid-Open Publication No. 170056/1986. The conventional cell has a base plate, a cylindrical container portion connected to the base plate for accommodating blood and a holder for holding the base plate therein as shown in FIG. 4 of the Publication. The hollow space of the cylindrical container portion is connected to an opening provided on the base plate. The holder in the form of a box has a holding spring for holding the base plate. In the holder are placed a slide glass and a packing plate. Further, the base plate is held on the packing plate by the holding spring.

When a liquid is separated into a liquid component and solid matter, the cell is placed in a centrifugal separator. When the centrifugal separator is operated, solid matter separated from a liquid to be processed, accommodated in the cylindrical container portion is attached to the slide glass. The remaining liquid component passes through the packing plate, because of its water permeability, into the holder and drops into the case of the centrifugal separator.

The holder of the conventional cell is made of metal to enable it to be used many times and the base plate and the cylindrical portion are also made so as to be repeatedly used. However, it is troublesome and ineffecitve to clean it after it is used and a sterilizing process is required after each cleaning.

SUMMARY OF THE INVENTION

It is an object of the present invention to provide a cell for placing solid matter on a slide glass under a centrifugal force which is disposable to avoid troublesome cleaning after its use and which can be easily assembled.

According to this invention, there is provided a cell for placing solid matter in a liquid on a piece of slide glass under a centrifugal force which comprises: a cell portion formed by mold forming of synthetic resin and having a container for accommodating a liquid to be processed and an elastic base plate for supporting the container, a hollow space in the container being open to the back of the base plate; a box-like holder formed by mold forming of synthetic resin for holding the base plate of the cell portion therein with a packing plate with a hole in registration with an opening of the base plate and a piece of slide glass on which solid matter separated from a liquid component is placed or recovered, one end of the holder portion being engaged with one end of the base plate of the cell portion; and a hook mechanism formed between the other end of the base plate of the cell portion and the other end of the holder.

The nature, utility, and further features of this invention will be more clearly apparent from the following detailed description with respect to preferred embodiments of the invention when read in conjunction with the accompanying drawings briefly described below.

DETAILED DESCRIPTION OF THE INVENTION

Figure 1:
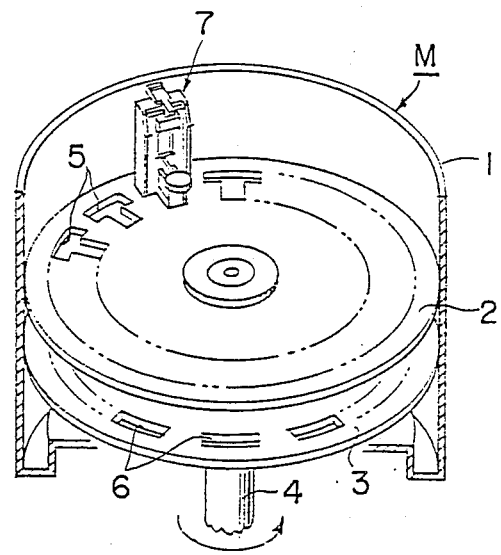
FIG. 1 is a perspective view, partially broken, of a centrifugal separator.

Referring to FIG. 1, a centrifugal separator M comprises a casing 1, an upper rotary plate 2, a lower rotary plate 3 and a rotary axis 4 to which the upper and lower rotary plates 2, 3 are fixed. The upper and lower plates 2, 3 have a plurality of holding openings 5,5, . . . ; 6,6, . . . disposed along their outer peripheries, respectively. Each pair of openings 5, 6 holds a cell 7 according to this invention.

Figure 2:
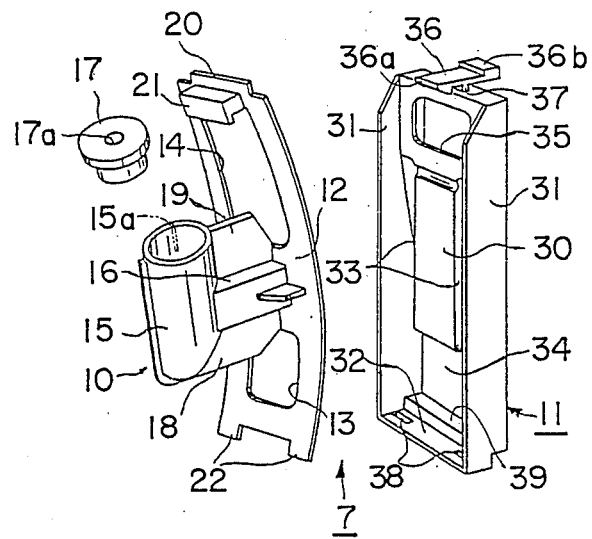
FIG. 2 is a perspective view of a cell according to this invention in a state wherein a cell portion is separated from a holder.
Figure 3:
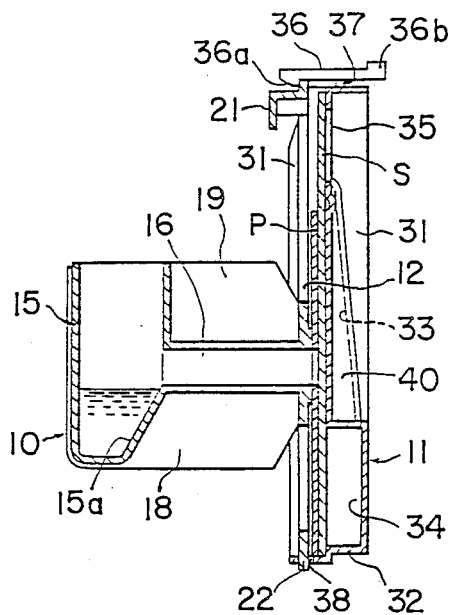
FIG. 3 is a vertical sectional view of the cell in a state wherein the cell portion is held in the holder.
Figure 6:
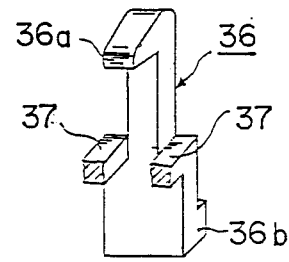
FIG. 6 is a perspective view of a hook.

The cell 7 has a cell portion 10 and a holder 11 as shown in FIGS. 2 and 3. The cell portion 10 comprises a base plate 12 having two openings 13, 14 and a cylindrical container 15 connected to the center portion of the base plate 12 through a connecting passage 16 extending perpendicular to the base plate 12. The cylindrical container 15 extends approximately parallel to the base plate 12. The bottom of the container 15 is closed while its upper portion is open. The bottom of the container 15 has an inclined surface 15a whose upper end terminates at the inlet of the connecting passage 16 and the upper opening 15a of the container 15 is covered with a cap 17. Further, the passage 16 is reinforced by two ribs 18, 19. The upper end of the base plate 12 has a projection 20 and a handle portion 21 while the lower end of the base plate 12 has two projections on both sides.

Figures 4, 5:
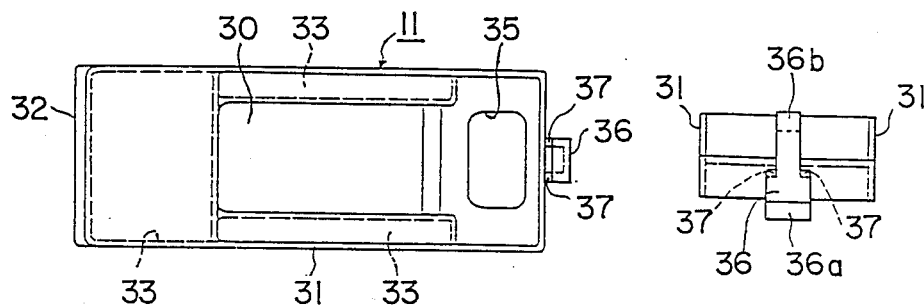
FIG. 4 is a bottom view of the holder.
FIG. 5 is a side view of the holder.

The holder 11 in the form of a box has a rectangular support plate 30 in its center portion on which a slide glass is laid, two side walls 31, 31 and a bottom end wall 32 as shown in FIGS. 2 to 4. On both sides of the support plate 30 are two slanting grooves 33, a recess 34 is provided on the lower side of the support plate 30. The liquid component of a liquid to be centrifugally processed flows into the recess 34 through the slanting grooves 33 during a centrifugal separating operation i.e. the slanting grooves 33 have bottoms sloping down from the upper side of the support plate 30 in the direction of the centrifugal force. A liquid penetrated through a slide grass enters into the slanting grooves and drops down along the bottoms of the slanting grooves into the recess 34 due to the centrifugal force and gravity force. On the upper side of the support plate 30 is formed an opening 35 through which a finger pushes the back of a slide glass when the slide glass is taken out of the holder 11. The upper end of the holder 11 has a swingable hook 36 for holding the projection 20 of the base plate 12 therein. The hook 36 is swingably supported on the upper end of the holder 11 by two connecting rods 37 as shown in FIGS. 2 to 6. The hook 36 has a hook portion 36a at its one end and has a tail 36b at its other end. The hook 36 is swung about the rods 37 by pushing the tail 36b and releasing it. On both sides of the bottom wall 32 are formed two slits 38, as shown in FIGS. 2 and 3, for receiving the respective projections 22 of the base plate 12.

The base plate 12 and the cylindrical container 15 are formed integrally with each other. These two members (cell portion 10) are made of nylon 66 to obtain a good molding characteristic, a high strength and elasticity while the holder 11 is made of polyethylene to obtain a good molding characteristic.

Figure 7:
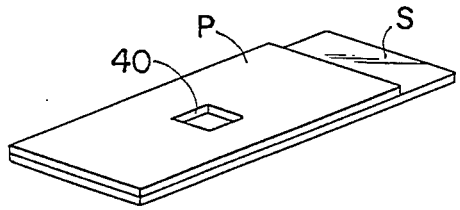
FIG. 7 is a perspective view of an arrangement of a piece of slide glass and a packing plate.

When the cell 7 is used, a slide glass S shown in FIG. 7 is placed in the holder 11 in a state wherein the upper part of the slide glass S is placed over the opening 35, the center portion thereof rests on the support plate 30 and the lower end thereof rests on a step 39 provided at the bottom of the holder 11. On the slide glass S is placed a packing plate P with water permeability in a state wherein a hole 40 of the plate P is registered with the opening of the passage 16 and further the base plate 12 is placed on the packing plate P in a state wherein the projections 22 provided at the bottom of the base plate 12 are inserted into the respective slits 38 of the bottom end wall 32. Then, the handle portion 21 of the base plate 12 is pushed by a finger toward the inside of the holder 11. At this time, the hook 36 is elastically deformed, that is, swung about the connecting rods 37. Thus, the projection 20 of the base plate 12 is engaged with the hook portion 36a of the hook 36.

The deformation of the base plate 12 is carried out mainly at two portions in which the two openings 13, 14 are formed and a portion between the two openings 13, 14 is not deformed. Accordingly, at the portion near the opening of the passage 16, the packing plate P is pressed uniformly on the slide glass S whereby solid matter in a liquid to be processed can be effectively prevented from flowing outside from the hole 40 of the packing plate P. An elastic force for pressing the slide glass S can be adjusted in such a manner that the thickness of the base plate 12 is changed, or that the size of the two openings 13, 14 thereof is changed. The cap 17 has at least one small hole 17a for air passage. Instead of the hole 17a, a narrow groove 15a may be formed on the inner surface of the opening of the container 15. The hole 17a or groove 15a functions to avoid a vacuum in the container 15 during a centrifugal operation.

After the cell portion 10 including a base plate 12 and the container 15 is assembled in the holder 11, a liquid to be processed is poured into the container 15 and the opening of the container 15 is then covered with the cap 17. The cell 7 is held vertically by the rotary plates 2, 3 and thereafter the rotary plates 2, 3 are rotated at a speed. Thus, the liquid is separated into two parts, e.g., a liquid component and solid matter under a centrifugal force. The solid matter is attached to the surface of the slide glass S, corresponding to the hole 40 of the packing plate P. The liquid component is pushed out from the opening of the passage 16 through the packing plate P with water permeability and flows into the recess 34 through the slanting grooves 33. If a filter element or sponge as sucking material is placed in the recess 34, the liquid component therein can be prevented from flowing out therefrom when the slide glass S is taken out from the holder 11. After the slide glass S with solid matter attached thereto is taken out from the holder 11, the cell 7 is thrown away.

Figures 8, 9:
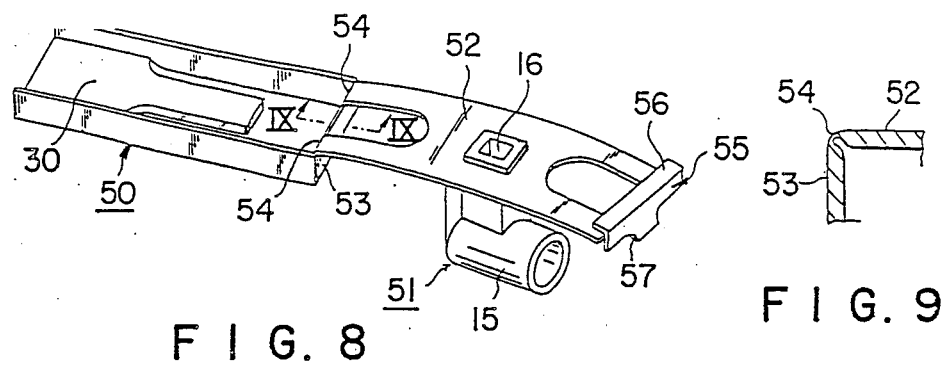
FIG. 8 is a perspective view of another embodiment of a cell.
FIG. 9 is a sectional view taken along the line IX—IX in FIG. 8.

FIGS. 8 and 9 show a second embodiment of this invention. A holder 50 and a cell portion 51 are formed integrally with each other in a state wherein one end of a base plate 52 is connected to one end wall 53 of the holder through a thin portion 54 functioning as a hinge. The base plate 52 has a hook 55 with a hook plate 56 and an elastic connecting member 57. Also in this cell, a slide glass and a packing plate are placed on the holder 50 and thereafter the base plate 52 is placed on the above two members. Further, the hook plate 56 is engaged with the bottom surface of the holder 50 thereby to join the cell portion 51 with the holder 50.

According to this invention, mass production of the cells is possible at a low cost by using synthetic resin molds thereby to make them disposable. Therefore, it is neither necessary to clean them any more after a centrifugally separating operation, nor to carry out a sterilizing process. Further, as a liquid component flowing out from a packing plate is effectively caught in a recess of a holder, dispersion of air-mist can be reliably avoided. Accordingly, even in case that poisonous material is contained in the liquid component, generation of dangerous condition can be avoided.

Figures 10, 11:
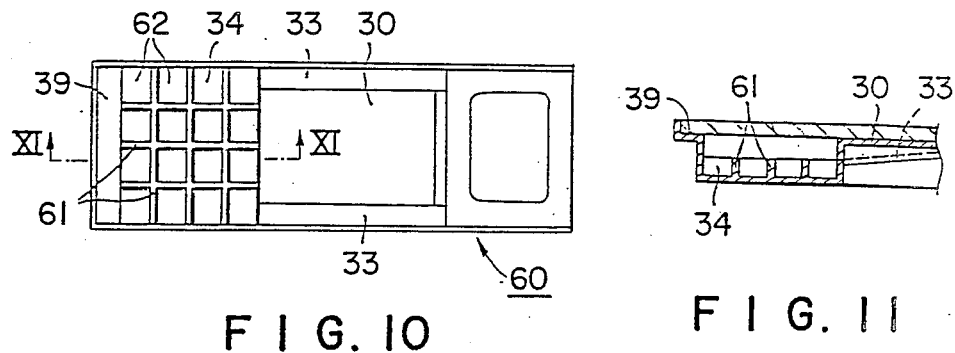
FIG. 10 is a plan view of another embodiment of a holder.
FIG. 11 is a sectional view taken along the line XI—XI in FIG. 10.
Figure 12:
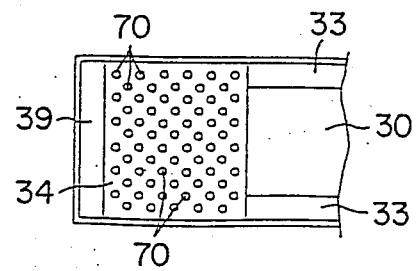
FIG. 12 is a plan view of a recess formed in a holder.

FIGS. 10 and 11 show another embodiment of a holder.

In the recess 34 of a holder 60 is integrally formed a lattice 61 which forms a plurality of rectangular spaces 62, for receiving or capturing a liquid component separated from solid matter in a liquid to be processed. The liquid component is reliably caught in the spaces 62 due to its surface tension. Accordingly, the liquid component can be prevented from flowing out from the holder 60 when the cell is taken out from the centrifugal separator M to recover a slide glass with solid matter thereon from the cell. Further, it is not required to place a sucking material for sucking the liquid component in the recess 34 of the holder 60.

Figures 13, 14:
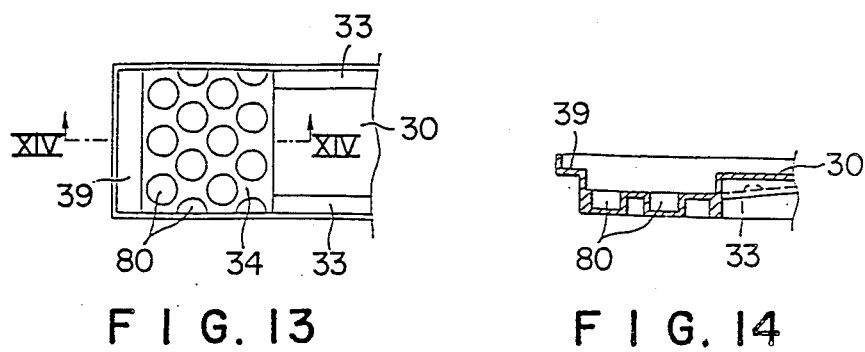
FIG. 13 is a plan view of another recess formed in a holder.
FIG. 14 is a sectional view taken along the line XIV—XIV in FIG. 13.

Instead of the lattice 61, a number of pins 70, may be integrally formed in the recess 34 in order to capture the liquid component therein. Further, a plurality of circular recesses 80, may be formed to capture the liquid component as shown in FIGS. 13 and 14.

Figure 15:
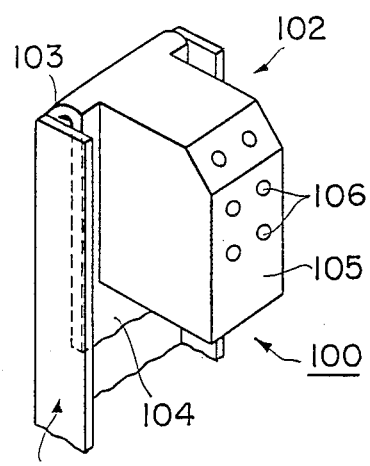
FIG. 15 is a partial perpsective view of still another embodiment of a cell.
Figure 16:
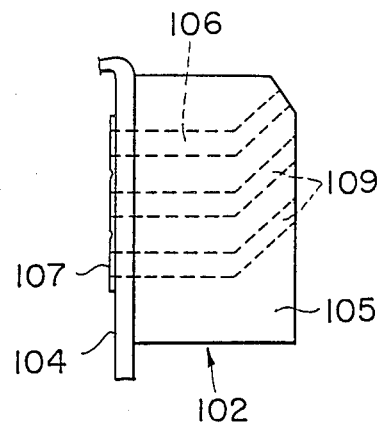
FIG. 16 is a side view of the cell portion of the cell shown in FIG. 15.
Figure 17:
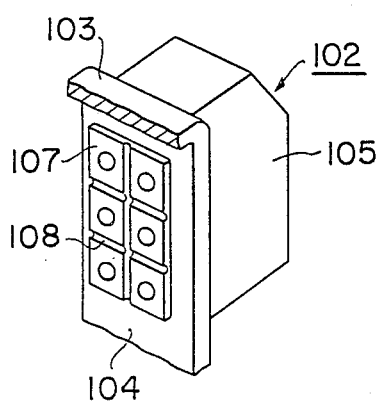
FIG. 17 is a back view of a cell portion of the cell shown in FIG. 15.

FIGS. 15 to 17 show another embodiment of a cell according to this invention.

A cell 100 comprises a box-like holder 101 and a cell portion 102 formed integrally with the holder 101. The holder 101 and the cell portion 102 are connected to each other via an elastic connecting portion 103. The cell portion 102 has a base plate 104 and a container portion 105 in the form of a block. The container portion 105 has a plurality of independent holes 106, for accommodating liquid to be processed. The inner end of each hole 106 is formed in an inner plate 107 projecting inwardly from the inner surface of the base plate 104. On the inner plate 107 are provided a plurality of grooves 108, for preventing mixing of a certain liquid component flowing out from a certain hole 108 and other liquid component flowing out from an adjoining hole 108 on a packing plate. Different kinds of liquids to be processed are poured into the respective holes 106. The cell portion 102 is made of acrylic resin so that the level of each liquid can be seen from outside and some marks 109, for showing a standard level of each liquid are formed on one side wall of the container portion 105.

Figure 18:
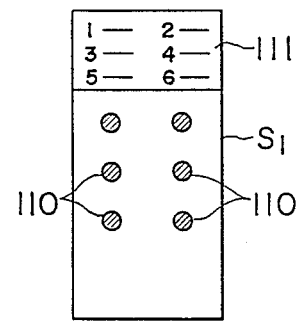
FIG. 18 is an elevational view of a piece of slide glass with a plurality of specimens thereon.

To the surface of a slide glass $S_1$ are attached different specimens 110, for a microscopic examination. The slide glass $S_1$ has a frosting surface 111 at its upper portion to write identification marks for the specimens 110 as shown in FIG. 18.

Between the base plate 104 of the cell portion 102 and the holder 101 is provided a hook mechanism which is similar to a hook mechanism shown in FIGS. 2 and 3. The cell portion 102 may be formed separately from the holder 101 in the same manner as shown in FIGS. 2 and 3.

Figure 19:
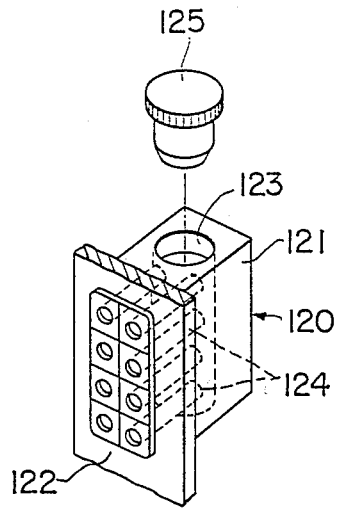
FIG. 19 is a perspective view of a modified cell portion.

The cell 102 is useful in processing a plurality of different liquids at the same time. However, when a plurality of specimens are prepared from a single kind of liquid, a cell portion 120 as shown in FIG. 19 may be useful. The cell portion 120 has a block-like container 121 and a base plate 122 and the container 121 is provided with a common vertical hole 123 from which a plurality of horizontal branch holes 124, are extended. A liquid in the common hole 123 is separately supplied to the surface of the slide glass through each branch hole 124. A cap 125 is engaged with the opening of the common hole 123.

What is claimed is:

1. A method of placing solid matter in a liquid on a slide glass with centrifugal force, the method comprising:

providing a cell portion having a container for accommodating solid matter in a liquid, an arcuate, elastic base plate connected to the container on one, concave, front side, the arc of the base plate extending between a bottom and an opposite, upper end of the base plate, and connecting-passage means connecting the container to means defining an opening in an opposite, convex, back side of the base plate for passage of the solid matter in the liquid from the container to the opening; and providing a box-like holder having holder bottom-end means on a bottom end of the holder;

engaging the holder bottom-end means with base-plate bottom-end means on the bottom end of the base plate with the back side of the base plate facing the holder;

elastically deforming uppermore portions of the arc of the base plate toward the holder to make the base plate less arcuate;

swinging a hook on an opposite, upper end of the holder for engaging hooking means on the upper end of the base plate when the holder and base-plate bottom-end means are engaged and the base plate is deformed toward the holder;

holding one side of a packing plate against the back side of the base plate with the elastic deformation of the base plate when the hook portion is engaged with the hooking means with means defining a hole in the packing plate registered with the opening in the back side of the base plate and holding one side of a slide glass against an opposite side of the packing plate; and rotating the cell portion and holder in a centrifuge to receive on the slide glass the solid matter in the liquid from the container passing through the connecting-passage means, opening and hole centrifugally.

2. A cell for placing solid matter in a liquid on a slide glass with centrifugal force, the cell comprising:

a cell portion having a container for accommodating solid matter in a liquid, an arcuate base plate connected to the container on one, concave, front side, the base plate having elastic means for making the base plate flexible and having an arc extending between a bottom end and an opposite, upper end of the base plate, and connecting-passage means connecting the container to means defining an opening in an opposite, convex, back side of the base plate for passage of the solid matter in the liquid from the container to the opening; and a box-like holder having holder bottom-end means on a bottom end of the holder for engaging base-plate bottom-end means on the bottom end of the base plate with the back side of the base plate facing the holder, whereby uppermore portions of the arc of the base plate can be elastically deformed toward the holder to make the base plate less arcuate, swingable-hook means on an opposite, upper end of the holder having a hook portion swingable for engaging hooking means on the upper end of the base plate when the holder and base-plate bottom-end means are engaged and the base plate is deformed toward the holder, slide-glass means for holding one side of a packing plate against the back side of the base plate when the hook portion is engaged with the hooking means with means defining a hole in the packing plate registered with the opening in the back side of the base plate and holding one side of a slide glass against an opposite side of the packing plate, whereby to receive on the slide glass the solid matter in the liquid from the container passing through the connecting-passage means, opening and hole centrifugally when the cell portion and holder are rotated in a centrifuge.

3. The cell according to claim 2, wherein: the base-plate bottom-end means comprises at least one first projection;

the holder bottom-end means comprises at least one slit corresponding to the at least one first projection for receiving the at least one first projection when the base-plate and holder bottom-end means are engaged;

the hooking means comprises a second projection; and the swingable-hook means comprises a connecting rod swingably connecting the hook portion to the holder with the hook portion projecting in one direction from the connecting rod and a tail portion connected to the hook portion and projecting in the opposite direction from the connecting rod for swinging the hook portion to the holder.

4. The cell according to claim 3, wherein the connecting-pasage means and opening are at a central portion of the base plate and the elastic means comprises first and second openings through the base plate respectively on opposite sides of the central portion of the base plate a direction between bottom and upper ends of the base plate.

5. The cell according to claim 4, wherein the slide-glass means comprises a support plate for supporting a central portion of an opposite side of the slide glass when the one side of the slide glass is held against the opposite side of the packing plate, a recess at the bottom end of the holder, first and second slanting-groove means extending in a direction between the bottom and upper ends of the holder and respectively on opposite sides of the support plate for allowing the liquid received on the slide glass to flow into the recess, whereby only the solid matter is retained on the slide glass, and means defining an opening into the holder at the upper end of the holder for facilitating removing the slide glass from the holder.

6. The cell according to claim 5, and further comprising capturing means in the recess for capturing the liquid flowing thereinto.

7. The cell according to claim 5, wherein the connecting-passage means and base plate opening each comprises a plurality holes for the passage of the solid matter in the liquid.

8. The cell according to claim 7, wherein the plurality of holes comprise a common hole and a plurality of holes branching therefrom.

9. The cell according to claim 2, wherein the connecting-passage means and opening are at a central portion of the base plate and the elastic means comprises means defining first and second openings through the base plate respectively on opposite sides of the central portion of the base plate in a direction between bottom and upper ends of the base plate.

10. The cell according to claim 9, wherein the holder and base-plate bottom end means are integral and, together, comprise an elastic connecting portion.

11. The cell according to claim 10, wherein the slide-glass means comprises a support plate for supporting a central portion of an opposite side of the slide glass when the one side of the slide glass is held against the opposite side of the packing plate, a recess at the bottom end of the holder, first and second slanting-groove means extending in a direction between the bottom and upper ends of the holder and respectively on opposite sides of the support plate for allowing the liquid received on the slide glass to flow into the recess, whereby only the solid matter is retained on the slide glass, and means defining an opening into the holder at the upper end of the holder for facilitating removing the slide glass from the holder.

12. The cell according to claim 11, and further comprising capturing means in the recess for capturing the liquid flowing thereinto.

13. The cell according to claim 11, wherein the connecting-passage means and base plate opening each comprises a plurality holes for the passage of the solid matter in the liquid.

14. The cell according to claim 13, wherein the plurality of holes comprise a common hole and a plurality of holes branching therefrom.

15. The cell according to claim 2, wherein the slide-glass means comprises a support plate for supporting a central portion of an opposite side of the slide glass when the one side of the slide glass is held against the opposite side of the packing plate, a recess at the bottom end of the holder, first and second slanting-groove means extending in a direction between the bottom and upper ends of the holder and respectively on opposite sides of the support plate for allowing the liquid received on the slide glass to flow into the recess, whereby only the solid matter is retained on the slide glass, and means defining an opening into the holder at the upper end of the holder for facilitating removing the slide glass from the holder.

16. The cell according to claim 15, and further comprising capturing means in the recess for capturing the liquid flowing thereinto.

17. The cell according to claim 2, wherein the holder and base-plate bottom end means are integral and, together, comprise an elastic connecting portion.

18. The cell according to claim 2, wherein the connecting-passage means and base plate opening each comprises a plurality holes for the passage of the solid matter in the liquid.

19. The cell according to claim 18, wherein the plurality of holes comprise a common hole and a plurality of holes branching therefrom.

20. A cell for placing solid matter in a liquid on a slide galss with centrifugal force, the cell comprising:
a container for accommodating solid matter in a liquid;
an arcuate base plate, the arc of the base plate extending between a bottom end and an opposite, upper end of the base plate, the base plate having means defining an opening in one, convex, back side of the base plate, elastic means for making the arc of the base plate elastic, base-plate bottom-end means on the bottom end of the base plate, and hooking means on the upper end of the base plate;
connecting-passage means connecting the container to an opposite, concave, front side of the base plate for centrifugal passage of the solid matter in the liquid from the container to the opening;
a box-like holder;
holder bottom-end means on a bottom end of the holder for engaging the base-plate bottom-end means with the back side of the base plate facing the holder, whereby uppermore portions of the arc of the base plate can be elastically deformed toward the holder;
swingable-hook means on an opposite, upper end of the holder having a hook portion swingable for engaging the hooking means on the base plate when the holder and base-plate bottom-end means are engaged and the base plate is deformed toward the holder; and
slide-glass means for holding one side of a packing plate against the back side of the base plate when the hook portion is engaged with the hooking means with means defining a hole in the packing plate registered with the opening in the back side of the base plate and holding one side of a slide glass against an opposite side of the packing plate, whereby to receive on the slide glass the solid matter in the liquid from the container passing through the connecting-passage means, opening and hole centrifugally when the cell portion and holder are rotated in a centrifuge.

* * * * *